United States Patent [19]
Gay et al.

[11] Patent Number: 5,218,417
[45] Date of Patent: Jun. 8, 1993

[54] SYSTEM AND METHODS FOR MEASURING THE HAZE OF A THIN FILM

[75] Inventors: Robert R. Gay, Camarillo; Jean J. Hummel, Chatsworth, both of Calif.

[73] Assignee: Siemens Corporation, Iselin, N.J.

[21] Appl. No.: 628,743

[22] Filed: Dec. 17, 1990

[51] Int. Cl.⁵ ............................................. G01J 3/00
[52] U.S. Cl. .................................. 356/300; 356/326; 356/237
[58] Field of Search ............... 356/300, 326, 328, 431, 356/237; 437/168

[56] References Cited

U.S. PATENT DOCUMENTS

| | | | |
|---|---|---|---|
| 4,376,583 | 3/1983 | Alford et al. | 356/431 |
| 4,884,891 | 12/1989 | Borsboom | 356/446 |
| 5,116,781 | 5/1992 | Agostinelli et al. | 437/168 |

Primary Examiner—Davis L. Willis
Assistant Examiner—K. P. Hantis
Attorney, Agent, or Firm—Robbins, Dalgarn, Berliner & Carson

[57] ABSTRACT

The present invention relates to a system and methods for measuring the haze of a thin film, such as a transparent conductive film, deposited on a substrate by either the reflectance of light by the external surface or the scattering of light by the internal grain surfaces of the thin film. More particularly, the haze measuring system is operated fully under computer control. The control program guides an operator through a calibration procedure, then calculates the haze of a thin film by comparing the reflectance minima at a wavelength of 500 nm or the ratio of the reflectance amplitude at 500 nm to 800 nm to calibration standards.

7 Claims, 8 Drawing Sheets

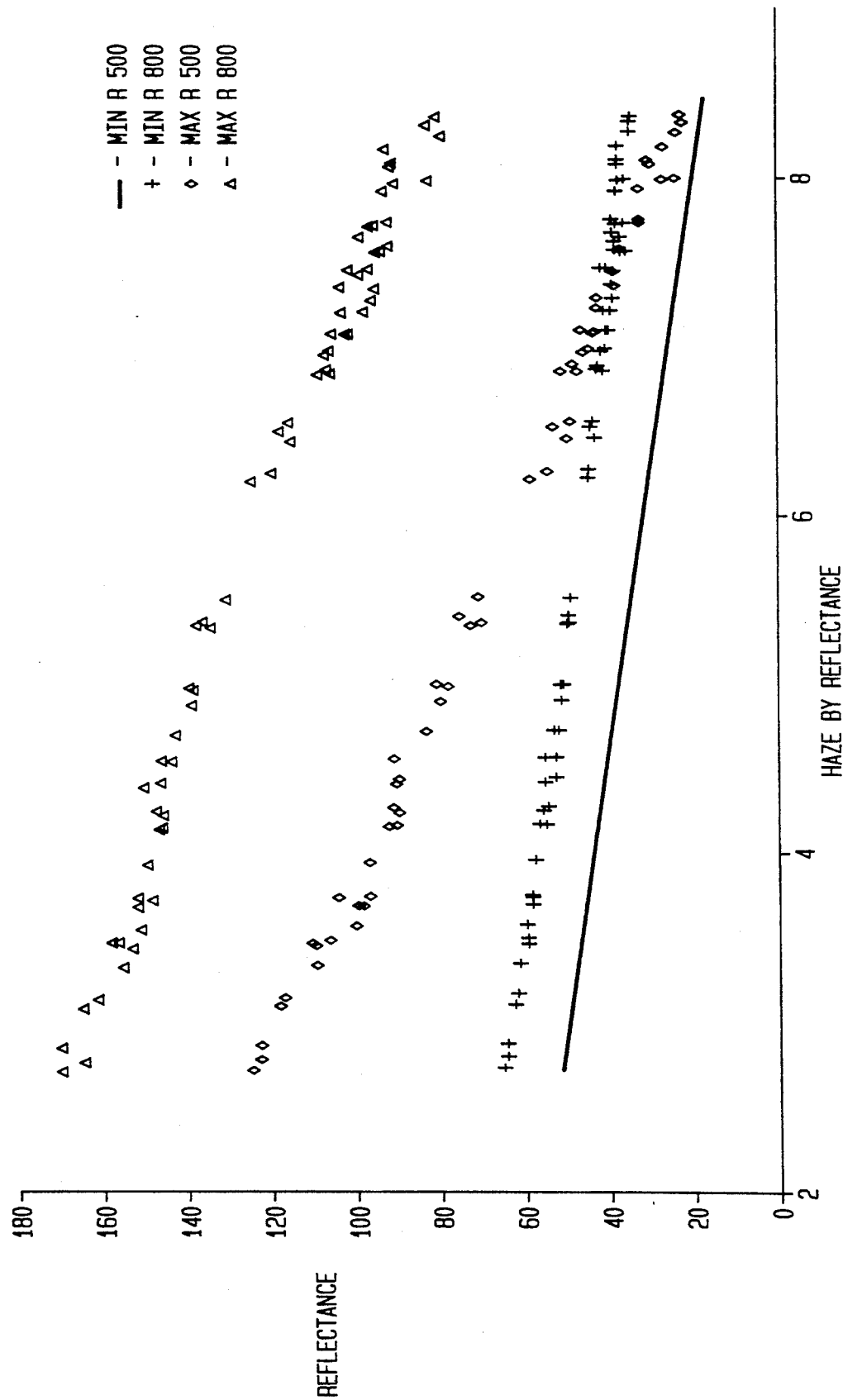

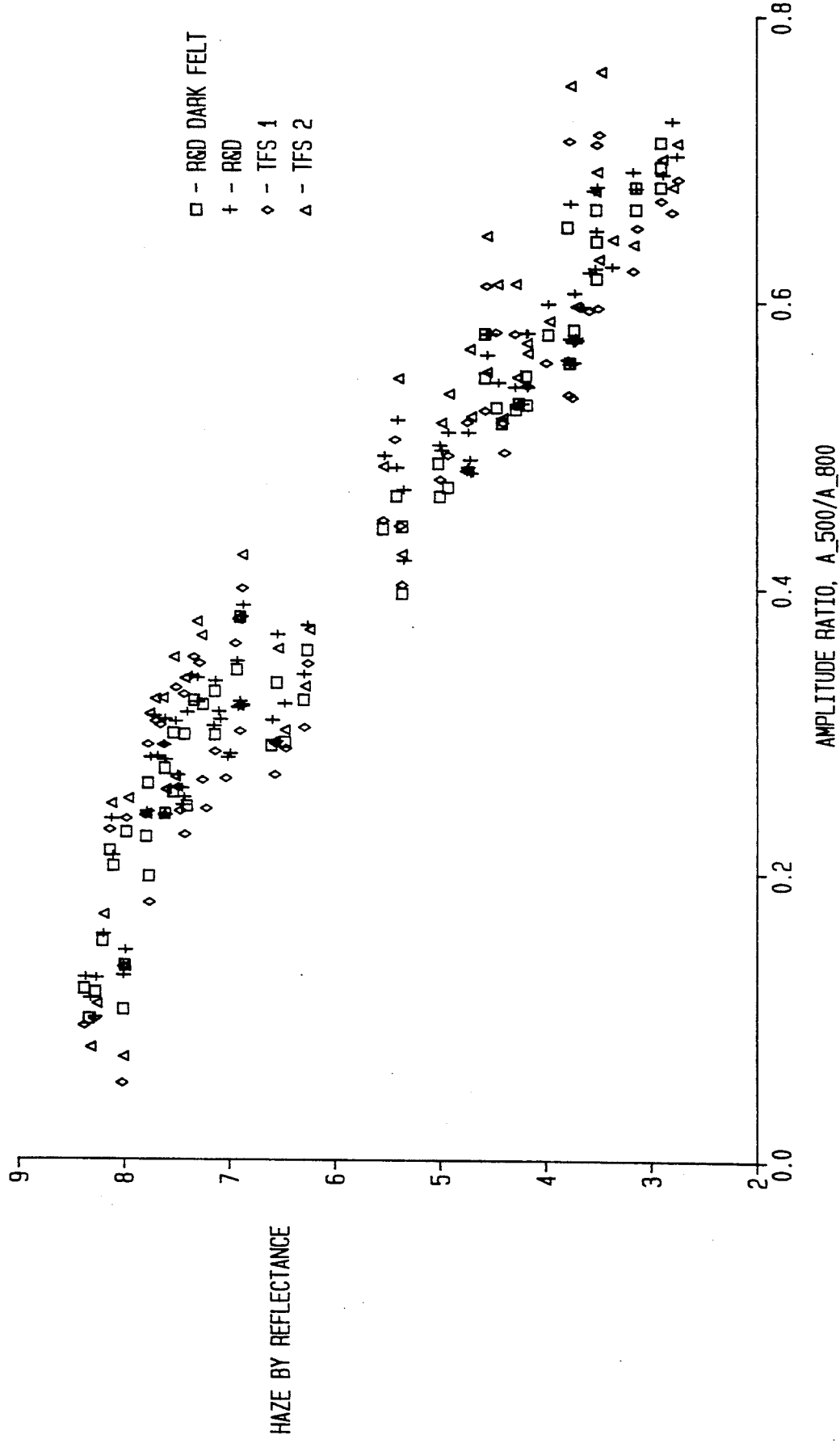

SYSTEM AND METHODS FOR MEASURING THE HAZE OF A THIN FILM

BACKGROUND OF THE INVENTION

Technical Field

The present invention relates to a system and methods for determining the haze of a thin film deposited on a substrate. Particularly, the system and methods measure the haze of a thin film, such as a transparent conductive film deposited on a substrate, by either the reflectance of light by the external surface or the scattering of light by the internal grain surfaces of the thin film.

Conventionally, the word "haze" is defined as the ratio of the diffuse (i.e. scattered) component of transmitted light to the total amount of light transmitted by a thin film for the wavelengths of light to which the photodetector is sensitive. However, as used herein, the word "haze" means the macroscopically observable ability of a thin film to scatter, reflect or transmit light in reference to an arbitrary relative haze scale. The haze scale is established by setting 50-90 samples of ZnO of varying "haziness" against a black background, then based on their relative haziness to the eye of an observer, they are arbitrarily assigned a number between 1 and 10 with a resolution of 0.5. Coarse assignments of the sample are made first; then detailed decisions are made by side-by-side comparisons of the samples.

As used herein, the word "fringer" means an optical measurement system for measuring the thickness and haze of thin films based on the optical interference ("fringes") observed in the spectrum of light reflected or scattered from the thin film surface.

As used herein, the word "transparent conductor" means a thin film having a sheet resistance value useful for fabricating practical photoconductor devices and also exhibiting a peak optical transmission of greater than about 75% in the wavelength range to which the photoconductor is sensitive.

Description of Background Art

Photoconductors such as zinc oxide (ZnO) and tin oxide ($SnO_2$), have been widely used as transparent conducting electrodes in thin film solar modules. ZnO's wide application is due to its many unique properties, such as its wide optical bandgap of approximately 3.3 eV allowing it to transmit even shorter wavelengths in the "blue" solar spectrum. In addition, ZnO can be deposited at relatively low temperatures with little lattice damage, for example, by the chemical vapor deposition process disclosed in U.S. Pat. No. 4,751,149, the disclosure of which is hereby incorporated by reference. ZnO also has electronic properties such as electron affinity and work function suitable for making efficient heterojunctions with a compound semiconductor, such as copper indium diselenide (CIS). The electrical conduction of ZnO films can further be controlled by composition variations or by the addition of extrinsic dopants such as H, Al, Ga or B. In practical applications, such as in thin film solar modules, the optical transmission and the electrical conductance of ZnO must be simultaneously optimized.

Co-pending U.S. patent application No. 07/411,148 filed Sept. 22, 1989 and assigned to the same assignee as this application, the disclosure of which is hereby incorporated by reference, teaches that the optical coupling and anti-reflection properties of ZnO transparent conductors in photovoltaic devices, and in particular ZnO/CdS/CIS based solar cells, depend strongly on the ZnO film morphology and/or structure. By carefully tailoring the process for formation of the ZnO film and/or through appropriate post-formation treatments, films with similar peak optical transmissions and thickness, but significantly different morphologies and/or structure have been formed.

The morphology and/or structure of transparent conductor film such as ZnO may be characterized by the degree of macroscopic "haze" arising from reflecting and scattering of incident light by the microscopic surface topology and the bulk grain structure. Dramatic improvements in broad band photoresponse and photocurrent density in thin film semiconductor solar cells produced as a result of the degree of haziness of otherwise identical ZnO transparent conductor films have been reported. For example, hazy ZnO on CIS increases the photocurrent density 30% or more relative to specular ZnO on CIS.

Photocurrent density has been found to increase with increasing transparent conductor film haze. Measurements of the quantum efficiencies of ZnO/CdS/CIS cells incorporating hazy ZnO layers, for example, demonstrate that the transparent conductor morphology and/or structure affects the cell photoresponse across the entire optical response band of the junction, suggesting that changes in photocurrent are due to a reduction in front surface reflection and to increased optical scattering by the transparent conductor grain structure. It is further believed that the observed effects are of a general nature, i.e., for any compound semiconductor photovoltaic device without antireflection coatings, inclusion of a ZnO transparent conductor front electrode exhibiting haze results in an increase in collection efficiency of the device.

Thus, a simple, fast, efficient, reproducible and economical system for measuring haze is needed to correlate the haze of a thin film and the performance of resulting photovoltaic devices incorporating such films.

One commercial instrument to measure haze is the model NDH-20D Digital Haze and Turbidity Meter manufactured by Nippon Denshoku Kogyo Co., Ltd. of Japan. Another hazemeter is manufactured by Taiyo-Yuden which measures the average of a broad band response at a silicon detector from a white light (incandescent) source. Both of these hazemeters are limited by the sample size they can handle and the linearity of haze with $T_{diffuse}$ measurement.

Another commercial haze measurement method is based on a comparison by eye of a sample to a set of arbitrary haze standards. This method is only semiquantitative and clearly lacks the precision required for accurate measurements.

In addition, these commercial hazemeters are slow, generally performing only one measurement per minute, thus severely limiting their usefulness in production applications. Also, some commercial systems, such as the "eye" comparison system, require the full-time attention of an operator which is labor intensive and expensive.

Therefore, there is an urgent need for a system and a method that is simple, accurate, fast, efficient, reproducible and economical for determining the haze of a thin film.

SUMMARY OF THE INVENTION

Accordingly, the present invention provided an operator-independent measurement of the haze of thin films that correlates to current density of photoconductors incorporating such films.

The haze measurement of the present invention has the additional advantages of being non-destructive and capable of mapping a large area ($>33 \times 130$ cm) transparent conductor sample by measuring a small area (about 1 cm$^2$) within a large part. The analysis of the present method is also fast ($<1$ sec/measurement).

In addition, the present methods for haze measurement are much less sensitive to the thickness of glass or its surface finish and provide useful information for ZnO or SnO$_2$ on glass or CIS.

The haze measuring system has a console which provides a table surface for positioning a reference, or alternatively, a sample and a housing for an optic and electronic system. The optic and electronic system further comprises an electromagnetic beam source and means to guide the beam incident onto the reference or the sample whereby upon incidence of the beam on the reference or the sample, a signal from the reference or the sample is reflected through the guiding means onto a detecting system.

The detecting system further comprises means to convert the analog signal into digital format and transmit it to a data processing and control means that has input and output means for communicating with an operator. The data processing and control means also guides the operator through a preliminary start-up calibration step which comprises calculating the reflectance of the sample at a fixed wavelength or an amplitude ratio at two fixed wavelengths. The reflectance is then converted into a haze value by comparison with reflectance previously determined for calibration samples of which the relative haze values have been assigned.

These and other objects of the invention, as well as a fuller understanding of the advantages thereof, can be had by reference to the following description and claims.

BRIEF DESCRIPTION OF THE DRAWINGS

The above and other features of the present invention may be more fully understood from the following detailed description, taken together with the accompanying drawings, wherein similar characters refer to similar elements throughout and in which:

FIG. 5 shows the calibration curve correlating the Min-R-500, Min-R-800, Max-R-500 and Max-R-800 with the haze of thin films on a substrate;

FIG. 8 shows the calibration curve correlating the amplitude ratio (A-500/A-800) with the haze of thin films on a substrate.

DESCRIPTION OF THE PREFERRED EMBODIMENT

The present invention is based on the measurement of haze relating to the reflectance of light by the external film surface or the scattering of light by the internal grain surfaces of the thin film.

Zinc oxide layers were deposited using a chemical vapor deposition (CVD) apparatus and processed as disclosed in U.S. Pat. No. 4,751,149, the disclosure of which is hereby incorporated by reference. The apparatus and procedures employed in preparation of solar cell samples are essentially in accordance with the preparative method disclosed in co-pending U.S. Application Ser. No. 07/411,148, and references cited therein.

A Zenith solar cell has a front electrode made of ZnO, an active semiconductor layer made from thin film silicon (TFS), and a rear electrode made of ZnO. The doping level in the front ZnO film deposited in a TFS Zenith solar cell was varied while keeping the film thickness and other deposition parameters fixed to the extent possible, in order to measure the photoresponse of the device as a function of the haziness of the thin film sample.

Figure 1:
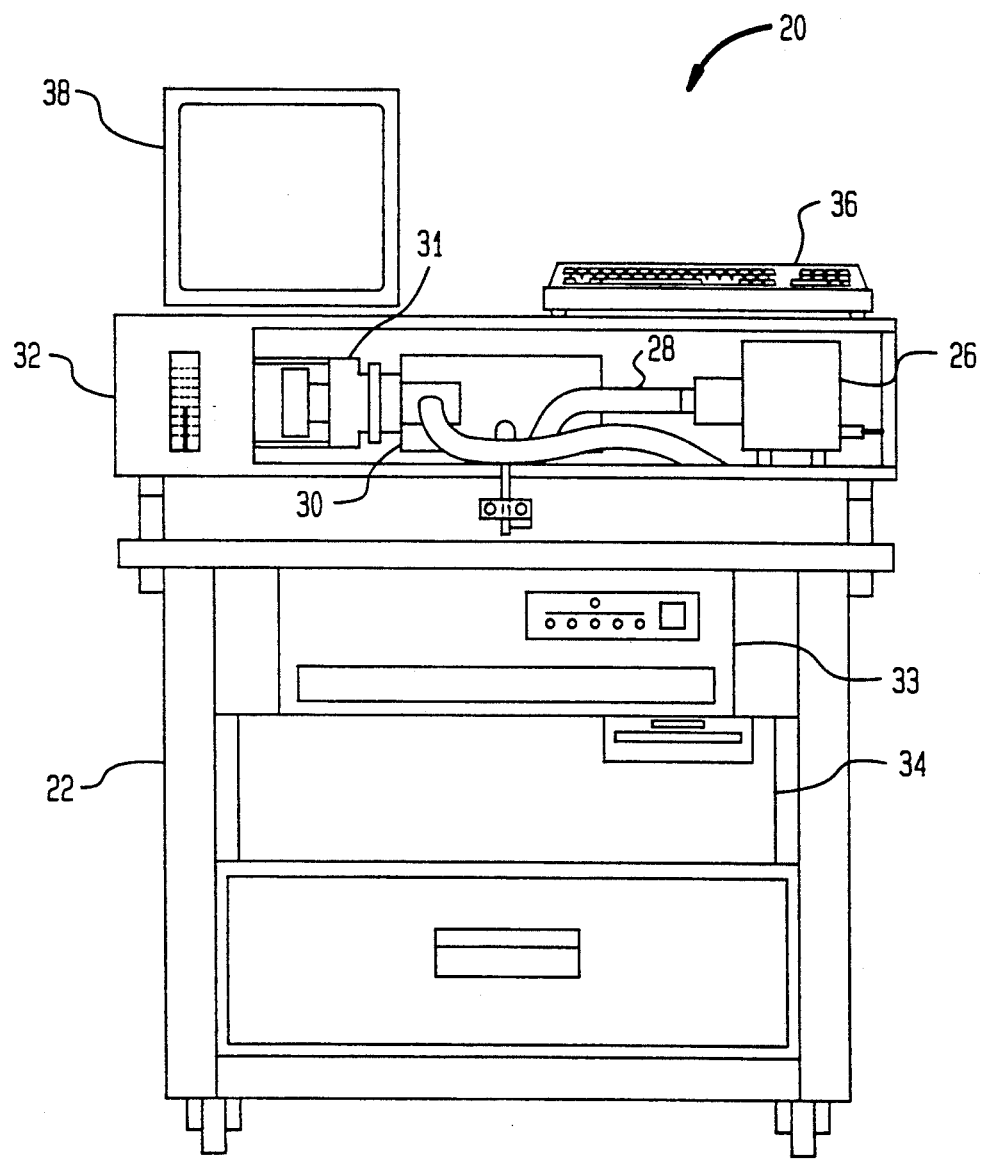
FIG. 1 illustrates a practical embodiment of the fringer system for measuring the haze of a thin film deposit on a substrate.

Referring now to FIG. 1, the configuration of the fringer system 20 is such that if additional equipment is needed it can be easily accommodated. The fringer 20 is a stand alone system. The complete fringer system has a console 22 which provides a table surface for positioning samples and a housing for the optics and electronics. The optics and electronics comprises a light source 26, such as an Oriel 200 W tungsten lamp, a light guiding and splitting means 28, fabricated of materials such as fiber optics and adapters, a light detecting system 30, such as an ISA flat field spectrograph with an EG & G Diode Array detector 31 and an inert gas (e.g. nitrogen) purging system 32. During operation, nitrogen is flowing at about 10 sccm to prevent condensation on the detector array 31 of the spectrograph 30. In addition, an interface 33, such as an EG & G diode array detector interface unit is used to acquire and convert the analog signals from the detector array 31 to digital form to be transmitted to the data processing and control unit 34, such as an IBM PC/AT computer system. The computer system 34 has input device 36, such as a keyboard, and output device 38, such as a NEC Multisync II monitor, to interact with an operator and guide him through the operation procedures of the system. Additionally, a mercury lamp is provided for calibration of the fringer system.

Figure 2:
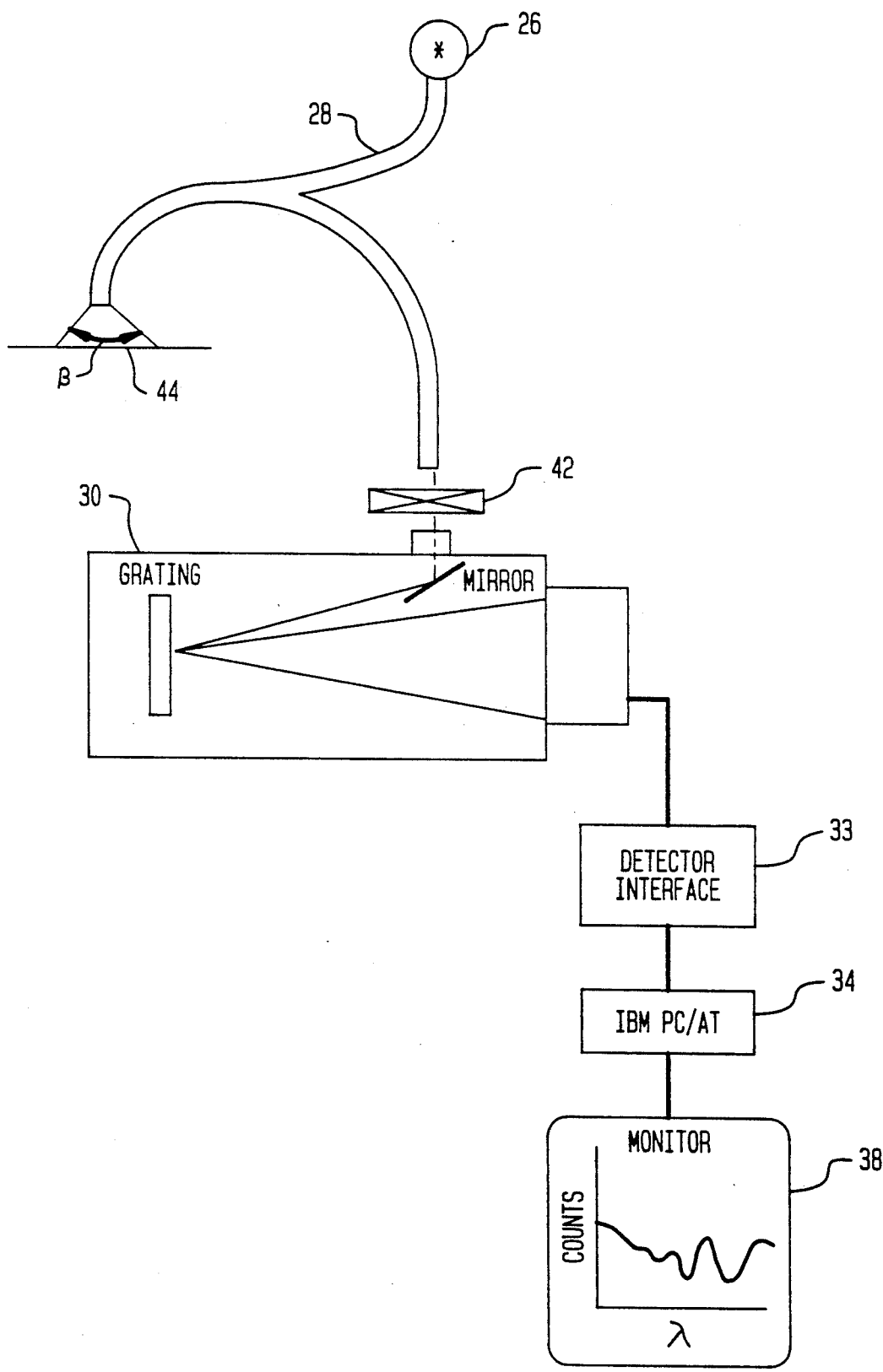
FIG. 2 illustrates the optical path of the practical embodiment of the fringer system.

FIG. 2 illustrates the optical path of the fringer system. As light is emitted from the source 26, fiber optics and adaptors 28 guide the light to the sample 44 at an optical acceptance angle B, generally about 25–66°. Portions of the beam incident on the reference or sample are reflected off both the top and bottom surfaces of the thin film reference or sample 44 and are guided through the Uniblitz shutter drive 42 onto the spectrograph 30.

The reflectance of the reference or sample is measured by the diode array 31 of the spectrograph 30. The analog reflectance signal is converted by the interface 33 into digital format and transferred to the control computer system 34 for analysis. The resulting spectrum is displayed on the monitor 38 for evaluation.

Figure 3:
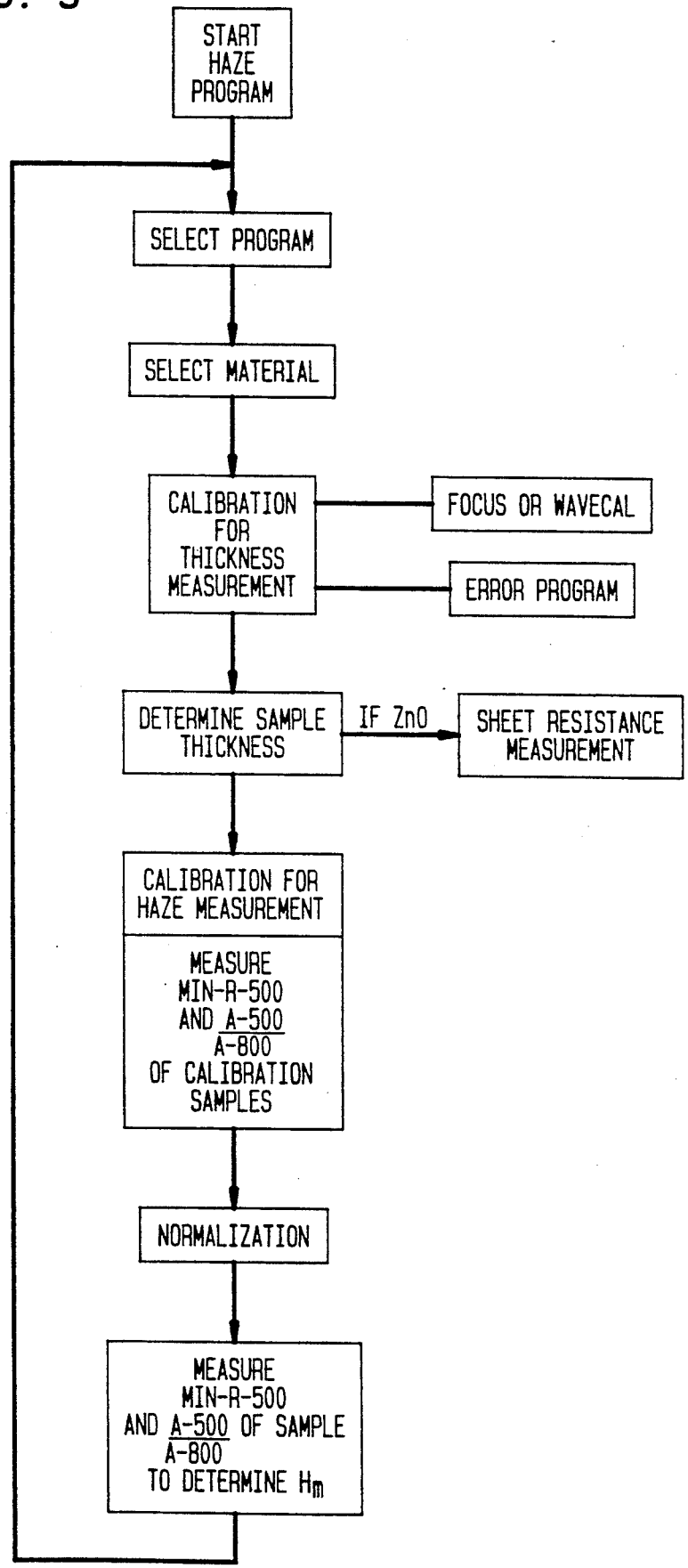
FIG. 3 is a flow chart of the fringer system's operating procedures.

The fringer system 20 is operated fully under computer control. As shown in FIG. 3, the control program guides the operator through a short calibration procedure, then instructs the operator to position a reference or sample under the light beam for measurement. The fringer system is meant for continuous operation and need only be turned off for servicing.

When the computer 34 boots up, the program for haze measurement is automatically loaded. An operator then presses any key to begin the program. The operator can select from the main menu either to start a test sequence, enter a live mode or a quit program. After the start test sequence has been selected, a choice of available materials will be displayed. The operator then selects the material from standard TFS (a-Si:H), tin oxide ($SnO_2$), cadmium sulfide (CdS), silicon nitride (a-Si:N:H), silicon carbide(a-Si:C:H), zinc oxide (ZnO) and red selenium (Se). After the proper material has been selected, the monitor 38 will display the "lamp set up procedure". A reference mirror which may be made of stainless steel or other material, depending upon the sample material selected, is first positioned under the fiber optics probe. The lamp voltage is then adjusted to properly fill the screen on the monitor 38. A key is then pressed to activate the computer into live mode in which live data from the detector 31 is displayed on the screen. The lamp voltage is continually adjusted by rotating the Variac TM knob on the front of the instrument until the spectrum of the thin film fills the screen. This spectrum is then stored as the reference spectrum. Once the fringer system has been properly calibrated, the sample 44 to be measured can then be placed under the beam.

The program is again activated and data for the sample spectrum will be gathered and the reflectance spectrum calculated. After measurement is completed, the full calculated reflectance spectrum showing the interference extrema (or "fringes") will be displayed, along with a message indicating the thickness of the sample. The thickness of thin film materials such as tin oxide and zinc oxide is generally about 1000Å–5 $\mu$.

Once the system has been calibrated, any number of samples can be measured. The measured thickness should agree with the reference sample to 2 nm. If it does not, two programs can be used to calibrate the spectrograph 30. A FOCUS program is used to adjust the focus of the spectrograph and a second program, WAVECAL, is provided to calibrate the wavelength of the calibration lamp.

The program also provides for error conditions, such as if the power to the interface 33 is not on, the error message "time limit exceeded" will be displayed. If the temperature of the detector 31 has not yet stabilized at 5° C., its standard operating temperature, another error message will be displayed. When the temperature of the detector is stabilized, the cooler locker light on the front panel of the interface 33 will turn on.

When the amount of signal coming from the sample 44 exceeds the ability of the instrument to reduce the exposure time, another error message will be displayed. The intensity of the lamp then must be reduced by reducing the voltage or by raising the height of the fiber optics probes 28 above the sample.

Using the same data as was used to determine the thickness of the thin films, the reflectance measurements are found to depend on the distance between the fiber optics probe 28 and the surface of the sample 44, the variations in the intensity of the source light 26 and the background, such as putting the sample 44 on a black felt or white paper.

Figure 4:
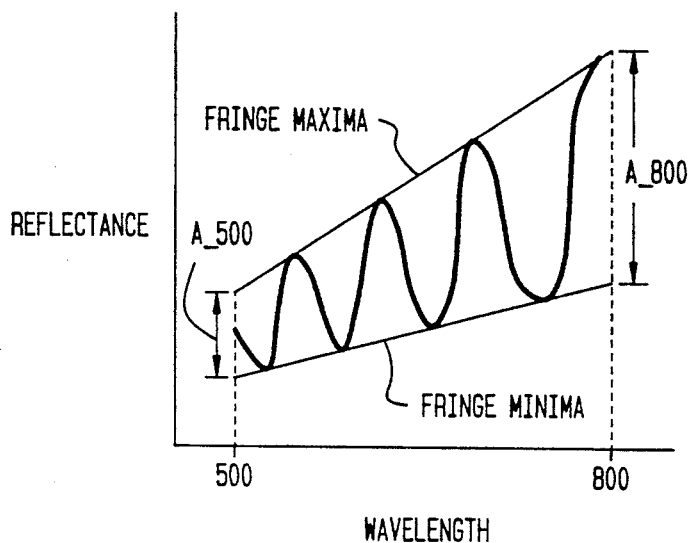
FIG. 4 shows the reflectance spectrum measured for a hazy thin film deposited on a substrate.

As shown in FIG. 4, the reflectance spectrum has a number of maxima and minima in the wavelength region of 450 to 850 nm due to interference. A linear least squares program is used to compute two lines which best fit the interference fringe maxima and minima respectively. The two lines were then used to calculate an effective reflectance value at 500 and 800 nm.

The standard condition for the fringer measuring haze is established to be with normal room lighting and the fringer probe in the center of the table. The tungsten lamp 26 is set to provide "full scale" count rates on the reference glass mirror and allowed 5 minutes to reach equilibrium. After every 10 samples, the reference glass mirror is used to calibrate the fringer system to eliminate errors due to drifting of the illumination from the source.

For haze calibration purposes, a set of reference samples, generally about 50–90, were prepared. A haze scale was then established by setting these samples against a black background and, based on their relative haziness to the eye of an observer, arbitrarily assigned a number between 1 and 10 with a resolution of 0.5. The target thickness in these runs is generally the same at about 2 $\mu$ and the haze varied with the amount of dopant $B_2H_6$ in the film, which in turn depends on the flow rate of the dopant gas during deposition of the film. The following definitions are used: Min R-500 500 as the reflectance minima value at 500 nm; Min-R-800 as the reflectance minima value at 800 nm; Max R-500 as the reflectance maxima value at 500 nm and Max R-800 as the reflectance maxima value at 800 nm.

The reflectance spectrum of the haze calibration sample sets are being measured in the wavelength region of 450–850 nm. It is found that all four reflectance parameters vary linearly with the haziness of the ZnO samples. However, due to different constructions and settings of different fringers, the absolute value of the reflectance measured is different for different fringers. Thus a normalization technique involving the performance of a linear fit for the reflectance data to the haze values is used to generate a set of calibration coefficients in order to translate the reflectance data from each data set to the reflectance haze.

The amplitude ratio is defined as:

$$\text{amplitude ratio} = \frac{A\text{-}500 = \text{Max } R\text{-}500 - \text{Min } R\text{-}500}{A\text{-}800 = \text{Max } R\text{-}800 - \text{Min-}R\text{-}800}$$

and is found to also show a linear correlation with the haze of thin films. Again, a normalization technique can be used to translate the amplitude ratio data from each data set to the reflectance haze by averaging the amplitude ratio measurements under different conditions. In addition, a linear fit of the amplitude ratio data to the haze is performed to generate a set of scale factors to convert the ratio data into haze numbers. A plot of the haze determined from the amplitude ratio versus the haze determined from the Min R-500 values is then performed.

Although the two techniques are internally self-consistent, they can differ from each other by as much as ±1.5 haze units. The fringer program provides measurements for haze by both methods. In the event the haze value determined by amplitude ratio is different from that determined by reflectance by more than 1 unit, the fringer system is recalibrated by measuring the reflectance of the reference glass mirror.

It will be readily apparent to those skilled in the art that a wide range of variations in the described haze measurement system would be suitable for use in accordance with the present invention. For example, voice recognition and activation devices instead of the keyboard as input devices are contemplated as within the scope of the invention. Alternatively, it is possible to use linear combinations of Min-R-500, Max-R-500, Min-R-800 and Max-R-800 to correlate with the haze of the thin film being measured in the fringer system.

The following non-limiting examples further illustrate the present invention. All measurements were performed with the fringer system.

EXAMPLES 1-70

A set of 70 ZnO sheets with varying $B_2H_6$ flow rates were prepared. A 10×10 cm sample was cut from each sheet and used for calibration runs. Each sample was marked with a circle in the center of the part and the thickness and haze were then measured using the fringer system. All samples were on textured glass of the same thickness, determined to be about $2\mu$. The haze for all 70 samples were measured under four conditions. First, the haze was measured with all the lights in the room turned off and each sample placed on black felt used for measurement with the reference glass mirror. Each sample was then measured again on the fringer table using standard lighting conditions. Two different fringer systems 1 and 2 were used for the measurements. The reflectances of the fringe minima and maxima at 500 and 800 nm were determined by a linear fit of the extrema between the two wavelengths. Using the first data set obtained with the lights off, a sample on felt and fringer system 1 used as the reference group, the calibration curves of haze in reference to Min-R-500, Min-R-800, Max-R-500 and Max-R-800 are shown in FIG. 5. As shown in FIG. 5, all four reflectance parameters vary linearly with the haze measured.

Figure 6:
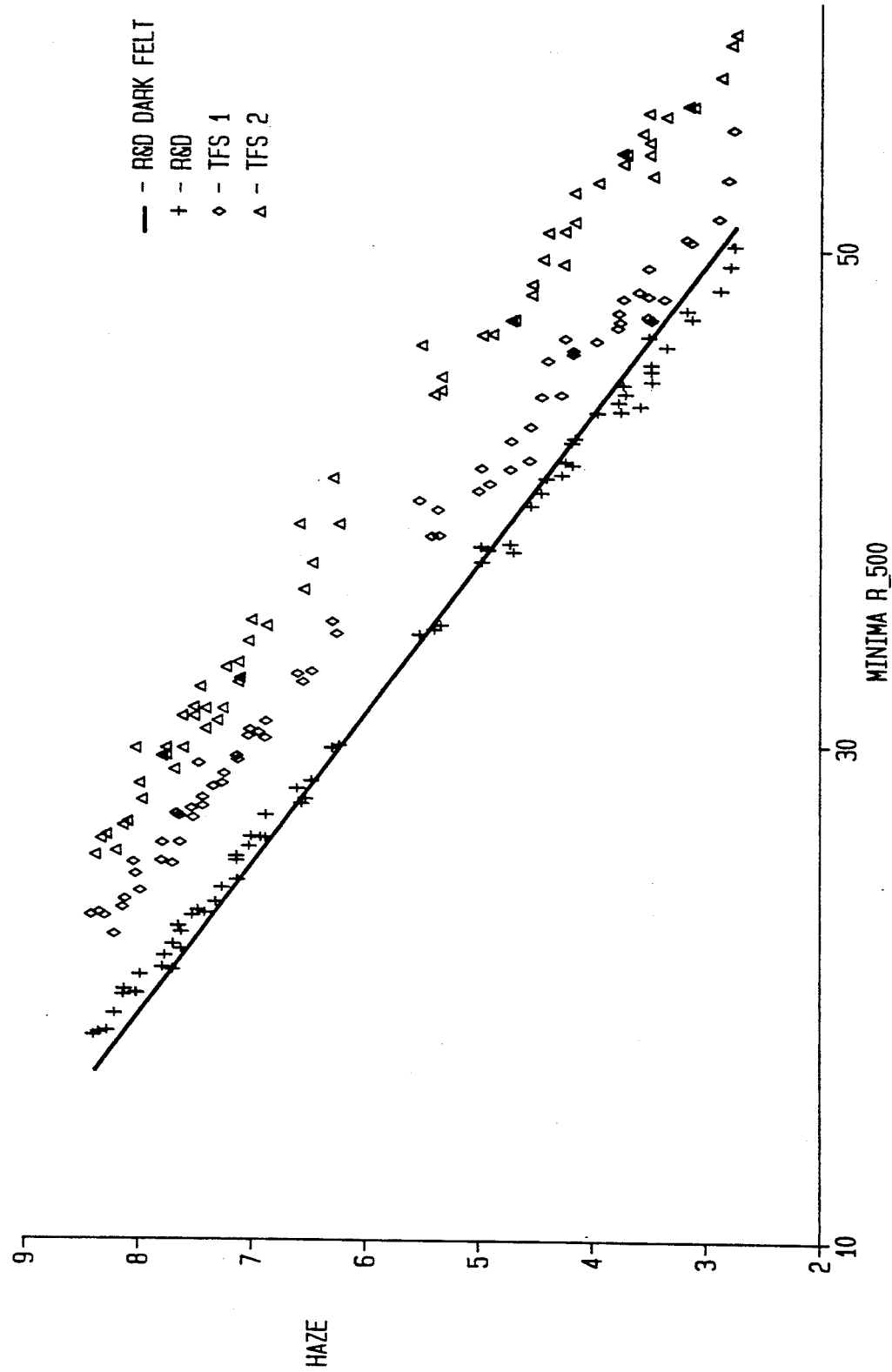
FIG. 6 shows the calibration curves correlating Min-R-500 measured at four different conditions with the haze of thin films on a substrate.
Figure 7:
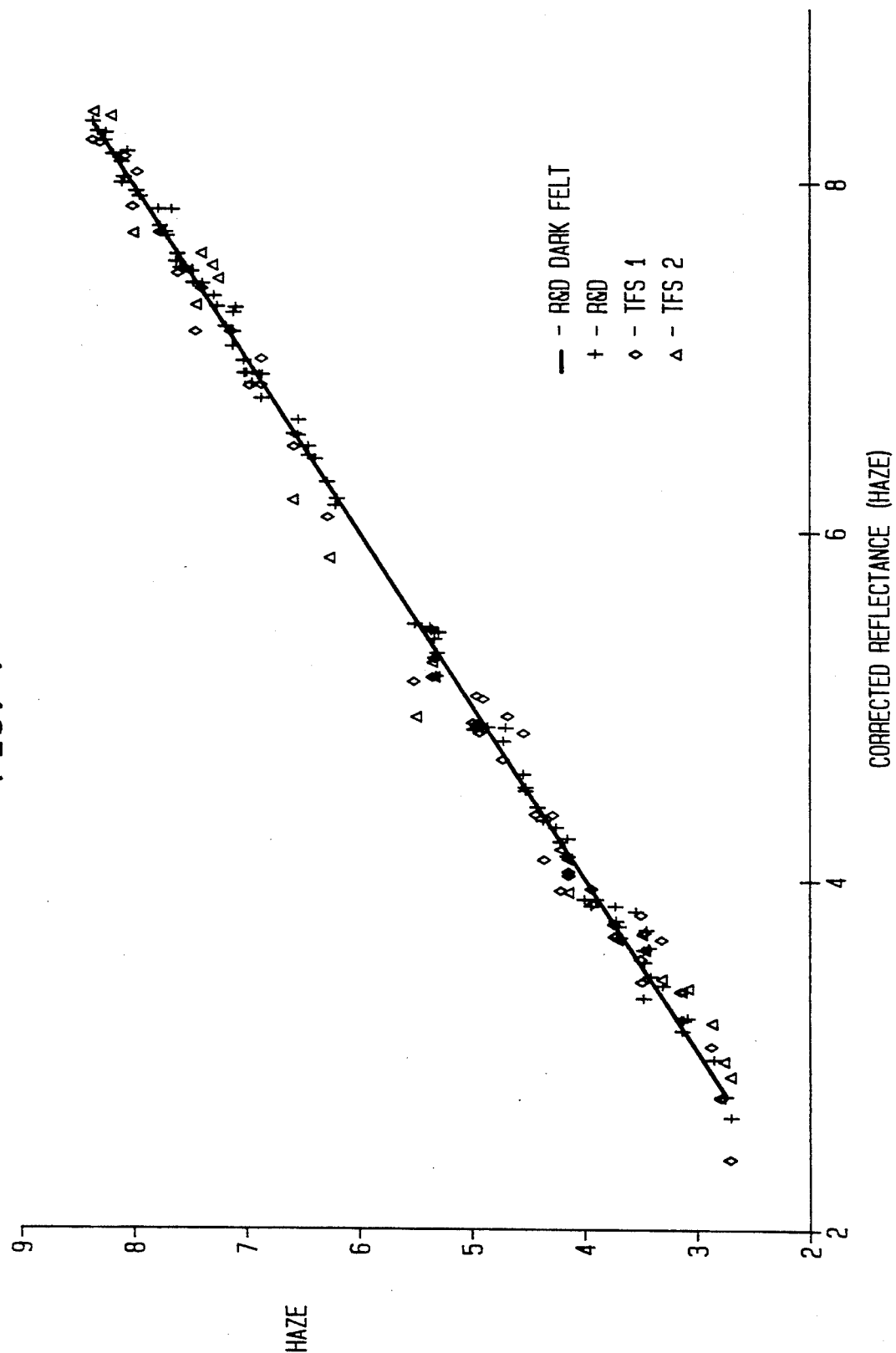
FIG. 7 shows the calibration curves of FIG. 6 after normalization.

The Min-R-500 versus haze scale is chosen for the reference scale. FIG. 6 shows the haze measured under the four conditions, all varying linearly with the reflectance to Min-R-500. Applying the normalization technique to the four sets of data as shown in FIG. 7, the four sets of normalized data merge together indicating the conditions of measurement only affect the absolute value of the haze but not its relative value. Thus, as long as the normalization technique is used, the reflectance data from each condition can be cross-compared to the other sets.

The amplitude ratio A-500/A-800 for the 70 samples were also determined and FIG. 8 shows a plot of the amplitude ratio versus haze for all four data sets. Again, excellent correlations were obtained for all four sets of data with the exception at high haze which is possibly due to the poor approximation of fitting the fringe extrema at high haze. Thus, the haze of a transparent photoconductor such as ZnO can be measured by either its minima reflectance at 500 nm or by the amplitude ratio.

EXAMPLES 71-76

Figure 9:
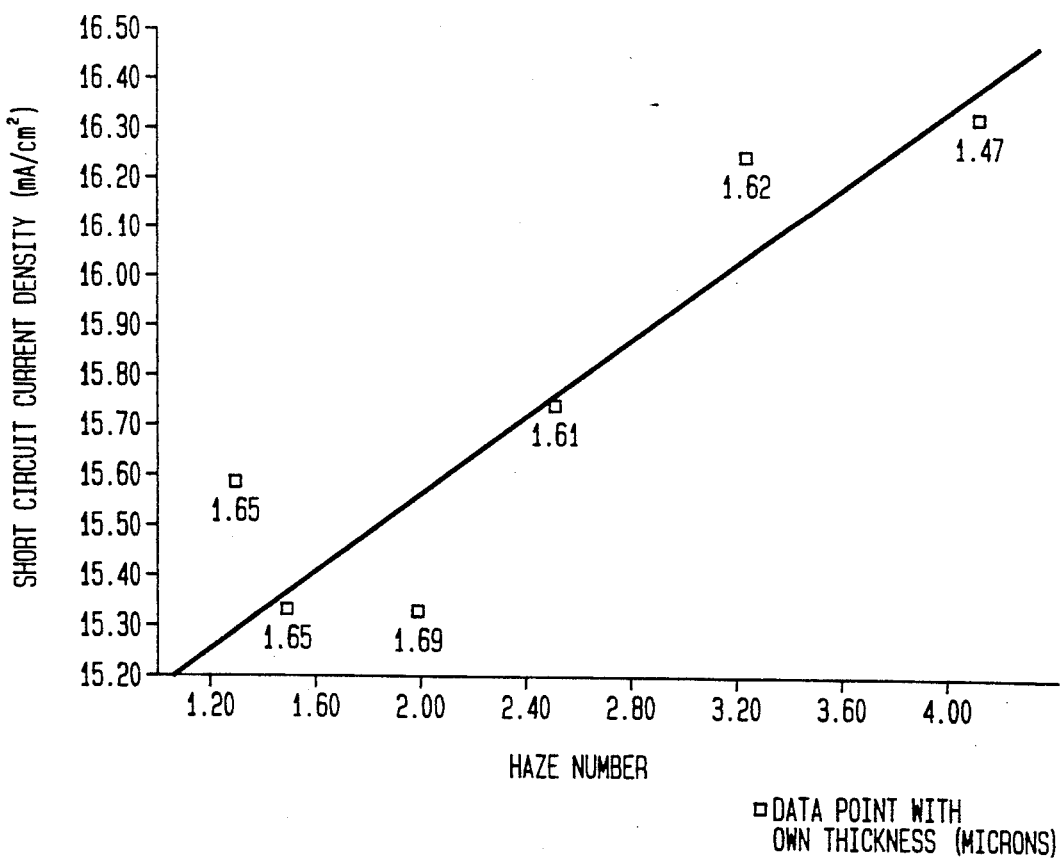
FIG. 9 illustrates the test results of short circuit current density of thin film silicon Zenith solar cells as a function of increasing haziness of the ZnO thin film.

After the calibration curve had been established, an experiment was performed to determine if these measurements of the haze correlated with currents in a TFS Zenith solar cell. For this experiment, six samples of ZnO were selected using the Fringer haze technique. The haze varied from 1.3 to 4.1. A solar cell structure using TFS was then prepared on all six samples in a single deposition so as to be as similar as possible. The thickness uniformity of the TFS is ±5%. The samples were then coated with a second deposition of ZnO, such that all samples received the same material with the same value of haze. The four reflectance properties of these devices were then measured using standard test methods. As shown in FIG. 9, a linear correlation between the short circuit current density and the haze of the front ZnO is observed.

The foregoing examples are intended to illustrate, without limitation, the system and method of the present invention, their use in determining and monitoring the haze of a thin film. It is understood that changes and variations can be made therein without departing from the scope of the invention as defined in the following claims.

We claim:

1. A haze measuring system comprising:
   positioning means on which a sample comprising a thin film of zinc oxide or tin oxide is positioned and
   an optic and electronic system, housed in said positioning means, for providing a measurement on said sample;
   said optic and electronic system further comprising:
   a source for generating a beam of electromagnetic radiation; said electromagnetic beam source further comprising a tungsten lamp; and
   means to guide said beam incident onto said sample whereby upon incidence of said beam on said sample, a returned beam from said sample is returned through said guiding means away from said source onto a detecting system;
   said detecting system further comprising:
   detector means for detecting said returned beam after incidence onto said sample and for providing an output signal representative of said returned beam;
   a data processing and control means connected to said detector means for processing said output signal;
   said data processing and control means having input and output means for communicating with an operator;
   said data processing and control means calculating reflectance of said sample at a fixed wavelength or calculating the extreme amplitude ratios at two fixed wavelengths; and
   said sample reflectance or amplitude ratio being converted by said data processing and control means to a haze value by comparison with reflectance or amplitude ratios previously determined for calibration samples of which haze values have been assigned.

2. The haze measuring system of claim 1, wherein further, said detector system comprises a spectrograph with a diode array.

3. The haze measuring system of claim 1, wherein further, said reflectance of said sample is calculated at a wavelength of 500 nm.

4. The haze measuring system of claim 1, wherein further, said reflectance of said sample is calculated at a wavelength of 800 nm.

5. The haze measuring system of claim 1 wherein further, said amplitude ratio is calculated for wavelengths of 500 and 800 nm.

6. A haze measuring system comprising:
- a substantially flat surface for positioning a sample and an optic and electronic system for providing a measurement on said sample;
- said optic and electronic system further comprising:
  - a tungsten lamp for generating a beam of electromagnetic radiation;
  - fiber optics for guiding said beam incident onto said sample and
  - whereby upon incidence of said beam on said sample, a signal from said sample is returned through said guiding means onto a detecting system;
- said detecting system further comprising:
  - a spectrograph with a diode array that can detect said signal;
  - an interface to convert said signal into digital format and transmit said signal to a computer system;
  - said computer system having input and output means for communicating with an operator;
  - after a thickness of said sample has been determined by said computer system, said computer system then calculating the reflectance of said sample at a wavelength of 500 nm or an extrema amplitude ratio at wavelengths of 500 and 800 nm;
  - said sample reflectance being converted by said computer system to a haze value by comparison with reflectance previously determined for calibration samples of which said haze values have been relatively assigned.

7. A method of measuring haze of a sample comprising the steps of:
- positioning a sample comprising a thin film of zinc oxide or tin oxide and an optic and electronic system housed in a positioning means for providing a measurement on said sample on a substantially flat surface;
- generating a beam of electromagnetic radiation from a tungsten lamp;
- guiding said beam incident onto said sample with fiber optics;
- returning a returned beam from said sample upon incidence of said beam on said sample through said fiber optics away from said source onto a detecting system;
- detecting said returned beam with a spectrograph with a diode array generating a signal;
- converting said signal into digital format and transmitting said signal by an interface to a computer system;
- communicating between an operator and said computer system through an input and output means;
- determining a thickness of said sample;
- calculating the reflectance of said sample at a wavelength of 500 nm or an extreme amplitude ratio at wavelength of 500 and 800 nm; and
- converting said sample reflectance to a haze value by comparison with reflectance previously determined for calibration samples of which haze values have been relatively assigned.

* * * * *